United States Patent [19]

Braier et al.

[11] Patent Number: 5,694,478
[45] Date of Patent: Dec. 2, 1997

[54] METHOD AND APPARATUS FOR DETECTING AND IDENTIFYING MICROBIAL COLONIES

[75] Inventors: Robert A. Braier, Woodbury; Scott D. Morgan, Cottage Grove, both of Minn.

[73] Assignee: Minnesota Mining and Manufacturing Company, St. Paul, Minn.

[21] Appl. No.: 356,484

[22] Filed: Dec. 15, 1994

[51] Int. Cl.$^6$ ................................................. G06K 9/00
[52] U.S. Cl. ........................... 382/133; 382/194; 435/808
[58] Field of Search .................... 382/128, 130, 382/133, 192, 194, 203; 435/39, 808; 364/413.07, 413.1; 356/39; 377/10, 11

[56] References Cited

U.S. PATENT DOCUMENTS

| | | | |
|---|---|---|---|
| 3,493,772 | 2/1970 | Daughters, II et al. | 250/222 |
| 3,736,432 | 5/1973 | Sweet | 250/222 PC |
| 3,757,299 | 9/1973 | Perry | 340/146.3 AC |
| 3,764,480 | 10/1973 | Jedlicka et al. | 195/103.5 R |
| 3,811,036 | 5/1974 | Perry | 235/92 PC |
| 3,972,778 | 8/1976 | Cunningham | 195/139 |
| 4,116,775 | 9/1978 | Charles et al. | 195/103.5 M |
| 4,118,280 | 10/1978 | Charles et al. | 195/127 |
| 4,456,380 | 6/1984 | Kondo et al. | 356/418 |
| 4,535,239 | 8/1985 | Brighton | 250/339 |
| 4,554,867 | 11/1985 | Thumm | 100/3 |
| 4,565,783 | 1/1986 | Hansen et al. | 435/299 |
| 4,637,053 | 1/1987 | Schalkowsky | 382/6 |
| 4,700,298 | 10/1987 | Palcic et al. | 364/414 |
| 4,720,463 | 1/1988 | Farber et al. | 435/291 |
| 4,724,543 | 2/1988 | Klevecz et al. | 382/6 |
| 4,896,966 | 1/1990 | Boisseau et al. | 356/442 |
| 4,922,092 | 5/1990 | Rushbrooke et al. | 250/213 VT |
| 5,003,611 | 3/1991 | Miyake et al. | 382/6 |
| 5,111,809 | 5/1992 | Gamble et al. | 128/204.18 |
| 5,117,467 | 5/1992 | Misaki et al. | 382/6 |
| 5,262,938 | 11/1993 | Rapoport et al. | 364/401 |
| 5,290,701 | 3/1994 | Wilkins | 435/312 |
| 5,510,246 | 4/1996 | Morgan | 435/39 |

FOREIGN PATENT DOCUMENTS

| | | | |
|---|---|---|---|
| 0 301 600 | 2/1989 | European Pat. Off. | G01N 21/59 |
| 2 602 074 | 1/1988 | France | G06F 15/62 |
| 24 43 410 | 10/1981 | Germany | G06M 11/02 |
| 39 16 804 | 11/1989 | Germany | C12Q 1/06 |
| 59-187777 | 10/1984 | Japan | C12M 1/34 |
| 62-60069 | 3/1987 | Japan | G06F 15/62 |
| 2-6729 | 1/1990 | Japan | G01N 15/14 |
| 2-55953 | 2/1990 | Japan | A61B 5/00 |
| 1434465 | 10/1988 | U.S.S.R. | G06M 11/02 |
| 2 227 346 | 7/1990 | United Kingdom | G06K 9/62 |
| WO 93/14599 | 7/1993 | WIPO | H04N 7/18 |
| WO 94/01528 | 1/1994 | WIPO | C12M 1/34 |

OTHER PUBLICATIONS

TEK TALK "Poultry processor finds automated microbiology system fast and accurate"; bioMerieux Vitek, Inc. (Winter, 1991).

Pocket Survival Guide; American Society for Microbiology; May 1992 bioMerieux Vitek.

Bactometer; "Systems rapides de bacteriologie automatisee pour l'industrie"; BioMerieux (No date).

(List continued on next page.)

*Primary Examiner*—Andrew Johns
*Attorney, Agent, or Firm*—Gary L. Griswold; Walter N. Kirn; James A. Rogers

[57] ABSTRACT

A method and system for detecting and identifying microbial colonies in an inoculated growth medium first acquires a first image of the inoculated growth medium. After a selected incubation time interval, a second image of the growth medium is acquired. A difference image is produced by taking the difference between corresponding pixels in the first and second images. Potential colonies are identified within the difference image by locating peak pixels having local maximum pixel intensities within the difference image and having decreasing gradients in a predetermined number of directions. The potential colonies are validated as actual colonies by eliminating those potential colonies that are noise spikes or noise around previously validated colonies.

32 Claims, 12 Drawing Sheets

OTHER PUBLICATIONS

Micro Bio Logie; Industrie et Environnement; bioMerieux (Nov. 1991), pp. 8–43.

"Ensemble, Servia La Vie" bioMerieux sa (No date).

"Bactometer—Rapid automated bacteriological systems for the industry"; bioMerieux, pp. 1–13 (No date).

"Counts Up to 1000 Objects in A Field, Automatically."; Artek Systems Corporation (no date).

Belyaev et al.; "Characterization of bacterial growth on solid medium with image analysis"; Journal of Biochemical and Biophysical Methods, 25 (1992) 125–132.

"Countermat Automation in Colony Counter"; IUL Instruments GmbH (no date).

"Colloque Microbiologie Industrielle—Resume des Interventions" bioMerieux (Mar. 31, 1992).

"Automates d'identification et d'antibiogramme"; VITEK; bioMerieux sa (Feb. 1991).

"ColonyImage—Digital Imaging Spectroscopy in your laboratory"; Kairos Inc. (no date).

"Investigacione Industrializacion" Formation Dialogue Bioscopie; bioMerieux sa (no date).

"The new I440F Power Scope—Quantitativ Fluorescence Imaging Microscopy"; Dipix Technologies Inc. (no date).

|   |   |   |   |   |   | 430 |   |   |   |   |   |
|---|---|---|---|---|---|---|---|---|---|---|---|
| 0 | 0 | 0 | 2 | 0 | 0 | 1 | 0 | 0 | 0 | 0 | 0 |
| 0 | 1 | 1 | 3 | 3 | 2 | 1 | 1 | 1 | 1 | 0 | 0 |
| 0 | 1 | 3 | 4 | 4 | 2 | 2 | 2 | 2 | 1 | 1 | 0 |
| 0 | 1 | 2 | 4 | 5 | 3 | 4 | 3 | 3 | 2 | 1 | 0 |
| 0 | 1 | 3 | 4 | 5 | 6 | 6 | 4 | 3 | 1 | 1 | 0 |
| 0 | 1 | 2 | 4 | 6 | 6 | 5 | 5 | 3 | 2 | 1 | 0 |
| 0 | 1 | 2 | 4 | 5 | 7 | 8 | 6 | 4 | 3 | 1 | 0 |
| 0 | 1 | 2 | 3 | 4 | 6 | 6 | 4 | 3 | 2 | 1 | 0 |
| 0 | 1 | 2 | 3 | 4 | 5 | 5 | 3 | 3 | 2 | 1 | 0 |
| 0 | 1 | 2 | 2 | 3 | 3 | 3 | 3 | 2 | 2 | 1 | 0 |
| 0 | 1 | 1 | 1 | 2 | 1 | 1 | 2 | 1 | 1 | 0 | 0 |
| 0 | 0 | 0 | 0 | 1 | 0 | 0 | 1 | 0 | 0 | 0 | 0 |
*Fig. 13*
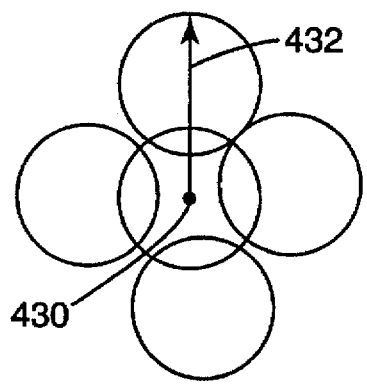
*Fig. 14*
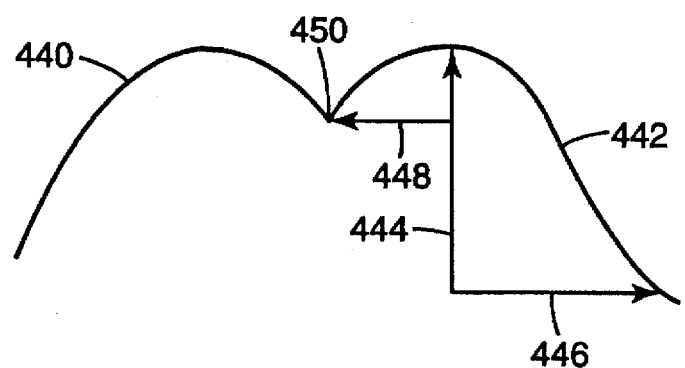
*Fig. 15a*
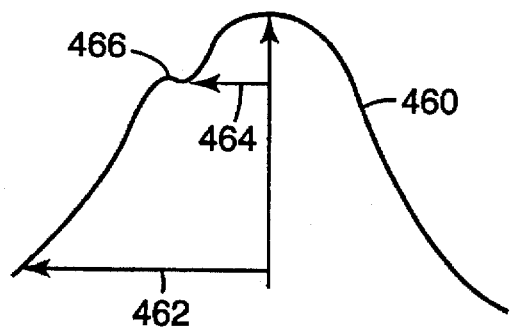
*Fig. 15b*

| NUMBER | PEAK VALUE | ROW | COLUMN | RADIUS | COMMENT |
|--------|-----------|-----|--------|--------|---------|
| 1 | 67 | 62 | 173 | 5 | DUST |
| 2 | 18 | 123 | 98 | 12 | OK |
| 3 | 12 | 167 | 128 | 9 | OK |
| 4 | 10 | 289 | 145 | 9 | OK |
| 5 | 6 | 221 | 192 | 7 | OK |
| 6 | 4 | 126 | 109 | 5 | EDGE OF #2 |
*Fig. 17*
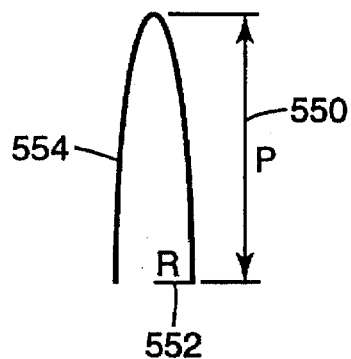
*Fig. 18*
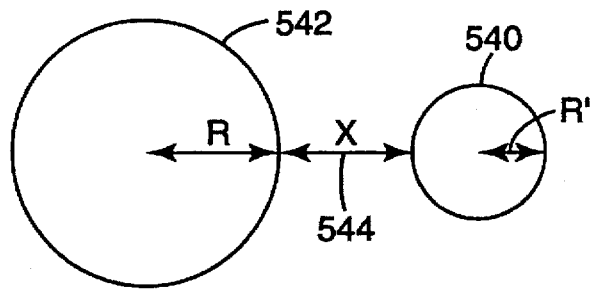
*Fig. 20*
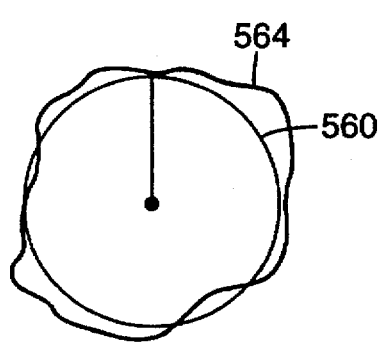
*Fig. 19*
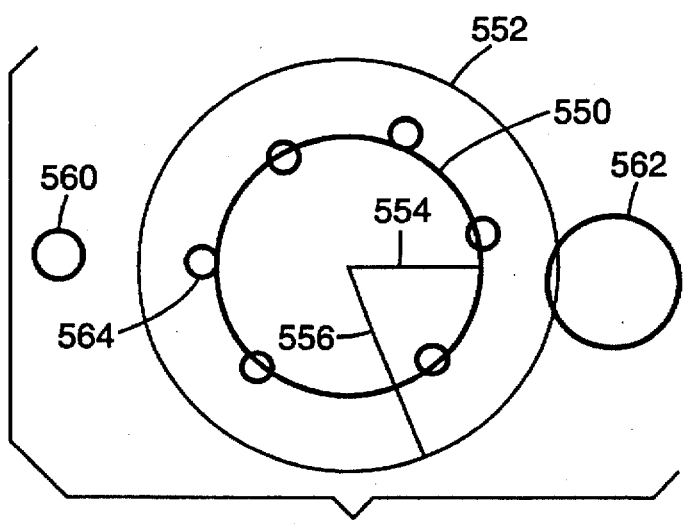
*Fig. 21a*

METHOD AND APPARATUS FOR DETECTING AND IDENTIFYING MICROBIAL COLONIES

FIELD OF THE INVENTION

The present invention relates generally to the automated detection and identification of microbial colonies on an inoculated surface. More particularly, the method and apparatus of the present invention provides for early detection and identification of microbial colonies by identifying and analyzing specified indicia of colony growth and monitoring the growth of the colonies.

BACKGROUND OF THE INVENTION

Many methods and apparatuses are used for counting microbial colonies in inoculated surfaces, such as in cultured petri dishes. One well known method of counting microbial colonies is manual counting of colonies by trained laboratory personnel. Typically, a culture plate device, such as a PETRIFILM thin film culture plate, manufactured by Minnesota Mining and Manufacturing Company, St. Paul, Minn., is inoculated with a particular sample, marked to identify the inoculant sample source, stacked together with similarly inoculated devices, and placed into an incubator. Manual inspection and counting is typically performed after approximately 24 hours. Manual counting has many disadvantages, including the cost associated with the used of skilled technicians to perform the time-consuming chore of counting, as well as the limited accuracy in the counts achieved.

Automated systems for counting microbial colonies are also known for providing confirmed total counts of fully incubated growth media, i.e., growth media that have been incubated for 24 hours or more. A first category of automated systems include systems employing cameras or video equipment in conjunction with hard wired circuits or digital computers to count levels in culturing devices by measuring total light absorption of the culturing devices. Examples of such systems are described in EP Publication No. 0 301 600; U.S. Pat. No. 3,811,036 to Perry; U.S. Pat. No. 5,003,611 to Miyake et al. and French Publication No. 2 602 074. These systems are designed to count colonies in culturing devices which have been incubated for at least 24 hours.

A second category of automated counting systems typically use an array of photodetectors and hard wired circuitry to perform the counting process. These systems typically provide signals which indicate that a colony is either existing or not existing. They do not supply information regarding the intensity of the colonies or their rate of growth between intervals. These systems are also designed to count colonies in fully incubated growth media.

It is often beneficial to be able to detect and count microbial colonies before the growth media has been fully incubated. For example, early detection is desirable when testing food products when determining contamination in the product. Typically, samples of the products are taken and culturing devices are inoculated and incubated for a period of 24 hours or more to determine the contamination level of the product. If the samples indicate excessive contamination, the product must often be discarded. Reliable early detection and quantification of excessive contamination in the range of 6 to 12 hours is desirable because it allows manufacturers to identify contaminated products early in processing, thereby avoiding additional expenses incurred in processing product that will be discarded and possibly contaminating additional product by running it through contaminated processing equipment.

Early detection can be performed manually by laboratory technicians, although there are disadvantages to having technicians perform the early detection. One indicator of early colony growth is the rate of growth or change between successive readings of the culturing devices. It is difficult, if not impossible, for a human technician to accurately gauge the rate of growth or to distinguish the minute changes in growth indicia for what could be hundreds of culturing devices. It is also typically more expensive to employ technicians to provide colony counts. Therefore, what is desirable is an automated counting system having the capability of early detection such that it can provide an early count of microbial colonies.

The aforementioned automated counting systems are designed to count colonies on a fully incubated culturing device, detect overall contamination levels in culturing devices by measuring total light absorption of the culturing devices or merely count colonies without measuring the intensity of the indicia of colony growth. Therefore, they do not provide an automated method for producing a reliably accurate count of microbial colonies.

Reliable early detection and counting, however, can be accomplished by monitoring minute changes in one or more specified indicia of colony growth. Such indicia can include indicators which are not visible to the human eye, such as acids or enzymes produced by microbial colonies during growth. One method that relies on changes in specified indicia of colony growth in the early stages of incubation to provide early detection of microbial colonies is described in commonly-assigned U.S. patent application Ser. No. 08/061,678 to Morgan, filed May 14, 1993. The Morgan method detects growing microbial colonies and follows the growth of the colonies over a period of time in order to enumerate the number of colonies growing on the medium. Multiple images are used such that data from sequential images are processed to improve the detection of colonies. Hit pixels are identified from the enhanced data set derived from sequential images. Each hit pixel exceeds a threshold value and has a decreasing gradient in at least two directions for a distance of two pixels. Finally, hit pixels are clustered to produce matrices which correspond to microbial colonies. The Morgan method further obtains a mask image at specific light wavelengths and identifies pixels in the mask image which lie outside of the growth medium, thereby preventing processing of pixels which lie outside the growth medium.

SUMMARY OF THE INVENTION

The present invention provides a method and system for detecting and identifying microbial colonies in an inoculated growth medium. After a first image of the growth medium is obtained, the growth medium is incubated for a selected time interval. After incubation, a second image of the growth medium is obtained. A difference image is produced from the first and second images by taking the difference between corresponding pixels in the first and second images. Potential colonies are identified within the difference image, each potential colony having a peak pixel and a colony radius. The potential colonies are validated as actual colonies by ensuring the potential colony is not a noise spike nor noise around the perimeter of a previously validated colony.

BRIEF DESCRIPTION OF THE DRAWINGS

The present invention will be more fully described with reference to the accompanying drawings wherein like reference numerals identify corresponding components, and:

FIG. 9 helps illustrate locating seed pixels;

FIG. 11 helps illustrate how the method in FIG. 10 finds a local maximum associated with a seed pixel;

FIG. 13 helps illustrate how the peak gradient test from FIG. 8 is applied to a difference image;

FIG. 14 shows how closely clustered colonies can result in incorrect radius measurements;

FIG. 15a and 15b illustrate how a noise value can help differentiate between two close colonies and a colony with noise;

FIG. 17 is a sorted list of potential colonies;

FIG. 18 shows a schematic side cross-sectional view of how dust appears in a difference image;

FIG. 19 shows an actual edge of a microbial colony and how the microbial colony is modeled by the system;

FIG. 20 helps illustrate how the closest validated colony to a potential colony is determined;

FIGS. 21a and 21b show a top and a side cross-sectional view of a validated colony and potential colonies attempting to be validated.

DETAILED DESCRIPTION OF A PREFERRED EMBODIMENT

In the following detailed description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The present invention provides a method and apparatus for detecting and identifying microbial growth on an inoculated surface. For example, the present method and apparatus may be used for enumerating coliform growth on a P2000 Coliform Count Plate, manufactured by Minnesota Mining and Manufacturing Company, St. Paul, Minn. Moreover, the present invention improves the processing speed over the prior art methods while also improving the accuracy of detecting microbial colonies. More specifically, the present invention accurately finds the true center of a microbial colony, tracks the size of the colony, discerns noise caused from the diffusion of acid produced by a colony from closely clustered colonies and accurately counts clustered colonies.

Figure 1:
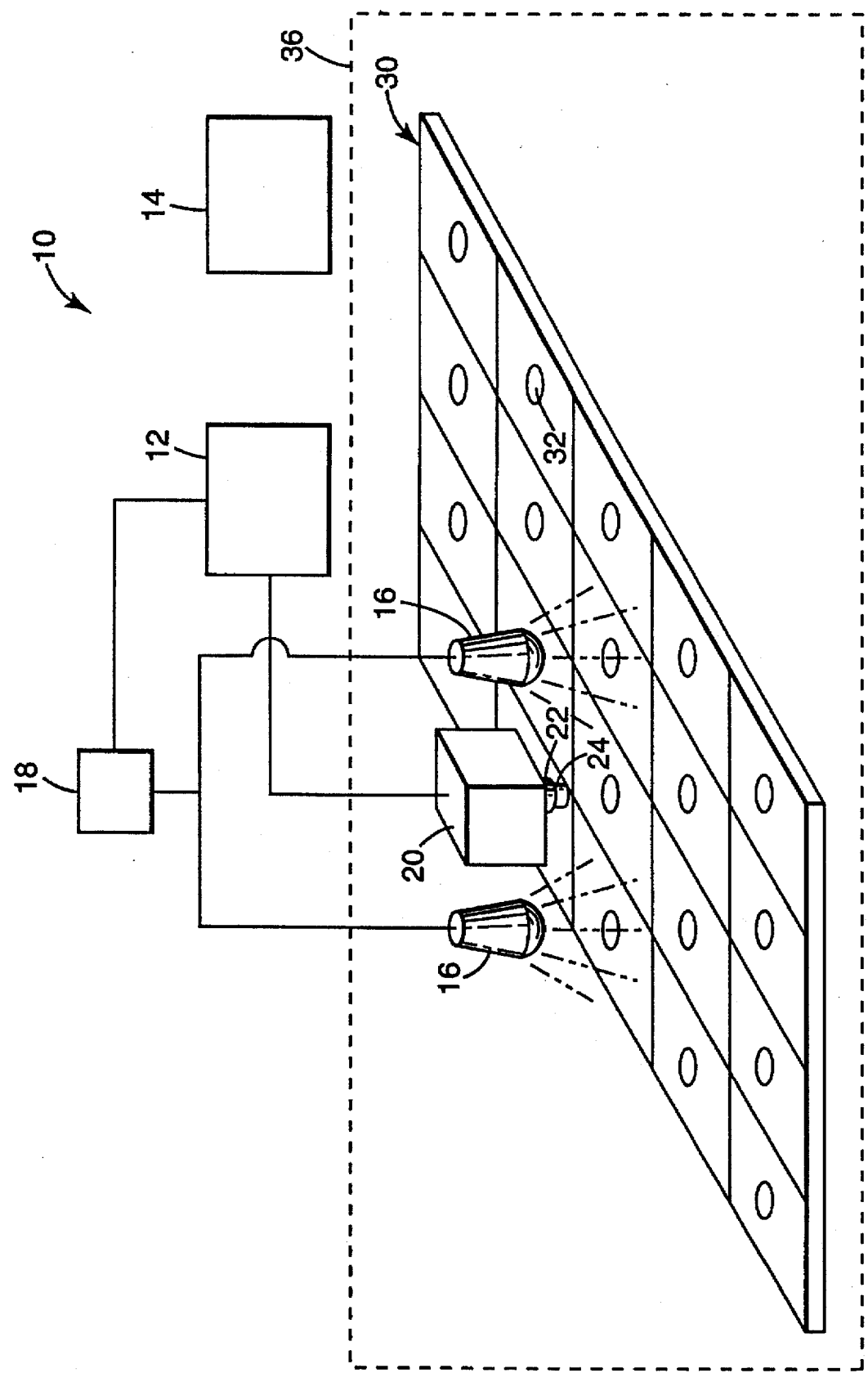
FIG. 1 is a schematic diagram of a preferred embodiment of the system for detecting and identifying microbial colonies on growth media.

Referring to FIG. 1, a schematic diagram of the system of the present invention is shown. To count microbial colonies in a nutrient media, such as agar, culture plate device 32, such as a petri dish or a disposable microbial culturing device, such as 3M brand PETRIFILM thin film culture plate, manufactured by Minnesota Mining and Manufacturing Company, St. Paul, Minn., is inoculated with a particular sample. For example, to test a sample for coliforms, P2000 PETRIFILM Coliform Count Plate, manufactured by Minnesota Mining and Manufacturing Company, would preferably be used for culture plate device 32. The preferred culture plate devices are designed to produce visible color change in regions of lower pH which surround a growing microbial colony. In the preferred plates, the color changes are produced by a phenol red coating placed in the culturing area of the plate which produces a yellow colored area on the red background in response to acids produced by coliforms, thereby allowing identification of the colonies. Those skilled in the art will readily recognize that other culturing devices could be used in place of the preferred plates for testing different types of microorganisms, with appropriate modifications to the imaging system that will later be described.

After inoculation with the material to be tested using standard inoculation procedures, culture plate device 32 is placed into incubation chamber 36, which provides heat to incubate culturing devices 32. Culture plate devices 32, may also be incubated using other means, such as heating blankets. In one embodiment, carrier 30 holds a plurality of culture plate devices 32. In another embodiment, separate holders are used for a plurality of culture plate devices 32. The use of carrier 30 allows system 10 to monitor a plurality of culturing devices 32. System 10 further includes a processor 12 and output device 14 such as a video display, printer or a memory device. Lights 16 provide lighting and are powered by power source 18. Camera 20 acquires images of culture plate 32 for processor 12 to process. A preferred camera 20 collects each of the images in a 512× 512 pixel array. The preferred camera 20 provides each image with 8 bits per pixel, resulting in each pixel being assigned a value from 0 to 255 based on the intensity of the light detected at each pixel. Pixels with a value of 0 correspond to a black object (returning substantially no light to the corresponding pixel in camera 20) and pixels with a value of 255 correspond to a completely white object (completely saturating the corresponding pixel in camera 20). With either carrier 30 or separate holders, a mechanical transport system, not shown, positions culture plate devices 32 such that all culture plates 32 may be imaged by camera 20. The mechanical transport system may be an x-y table or, more preferably, a stacking mechanism.

Camera 20 includes lens 22, which preferably is adjustable to obtain the desired field-of-view. Lens 22 further preferably includes filter 24. Because the preferred method involves the detection of specific wavelengths of reflected light, band-pass filters 24 may be interposed between camera 20 and culturing devices 32 to filter light reflected from culturing devices 32. For example, when coliform growth is to be detected on the red gelatinous media of a PETRIFILM P2000 Coliform Count Plate, a red band pass filter having a spectral peak at 650 nm and having a bandwidth of 40 nm is placed over lens 22. The image acquired by camera 20 will have high contrast between the red circular gel against the background of the foam dam surrounding the gel. Moreover, the red filter will eliminate most artifacts, such as voids that may be present in the gel.

Figure 2:
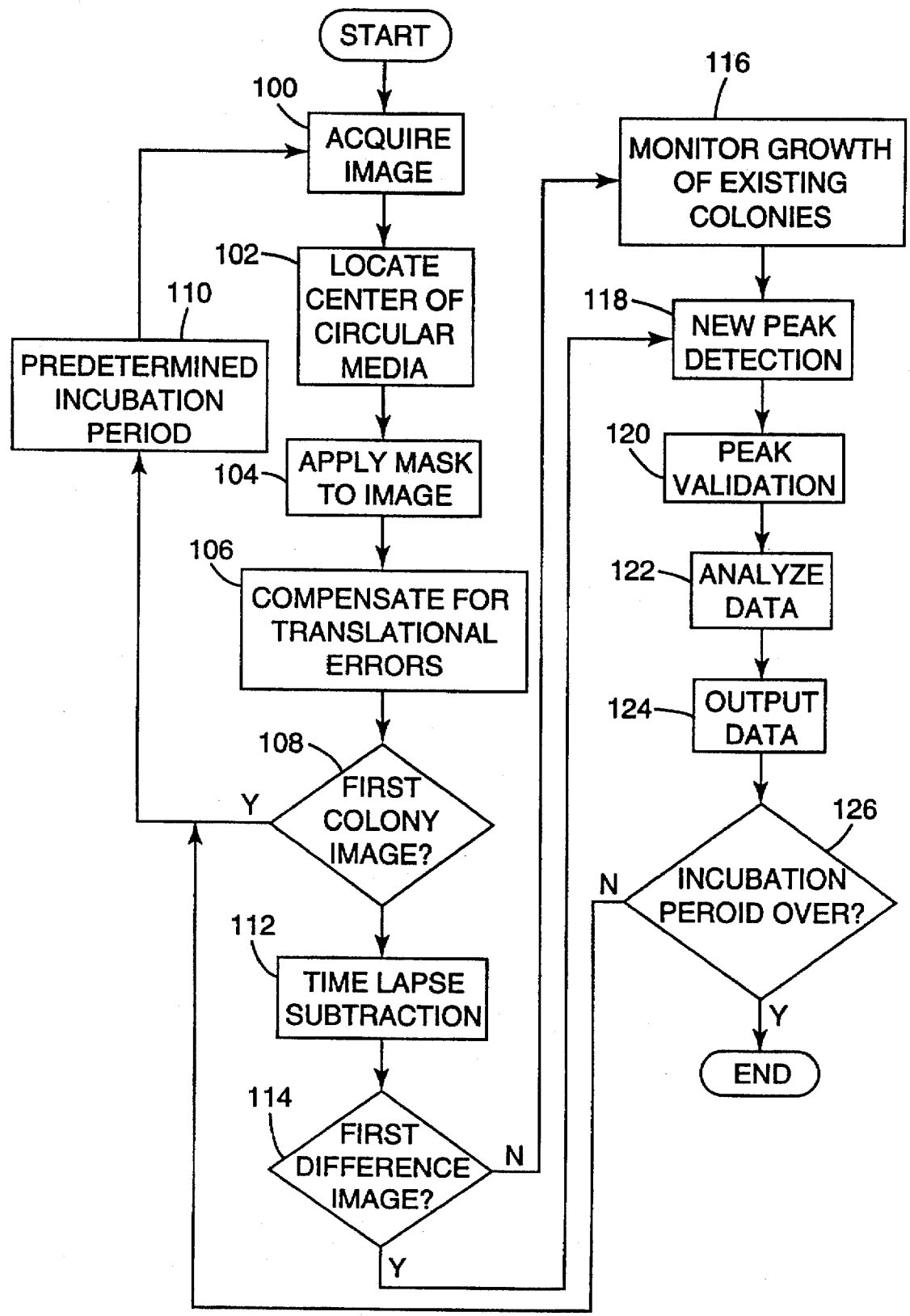
FIG. 2 is a flow diagram of a preferred method for detecting and identifying microbial colonies on growth media.

After culture plate 32 has been inoculated and placed in incubation chamber 36, camera 20 acquires an initial image of culture plate 32 as shown in block 100 in FIG. 2. In block 102, the center position of the circular gelatinous media of culture plate 32 is located. The center of the gelatinous media may vary from one culture plate to another due to variations in the manufacturing process. Further, when carrier 30 is used, a mechanical system typically is used to provide repeatable positioning of the culture plates such that camera 20 may monitor all culture plates on carrier 30. While the mechanical systems used with carriers typically are accurate to less than one pixel width in both the x and y directions, translational repositioning error may occur. Therefore, it is desirable to locate the true center of the media.

Figure 3:
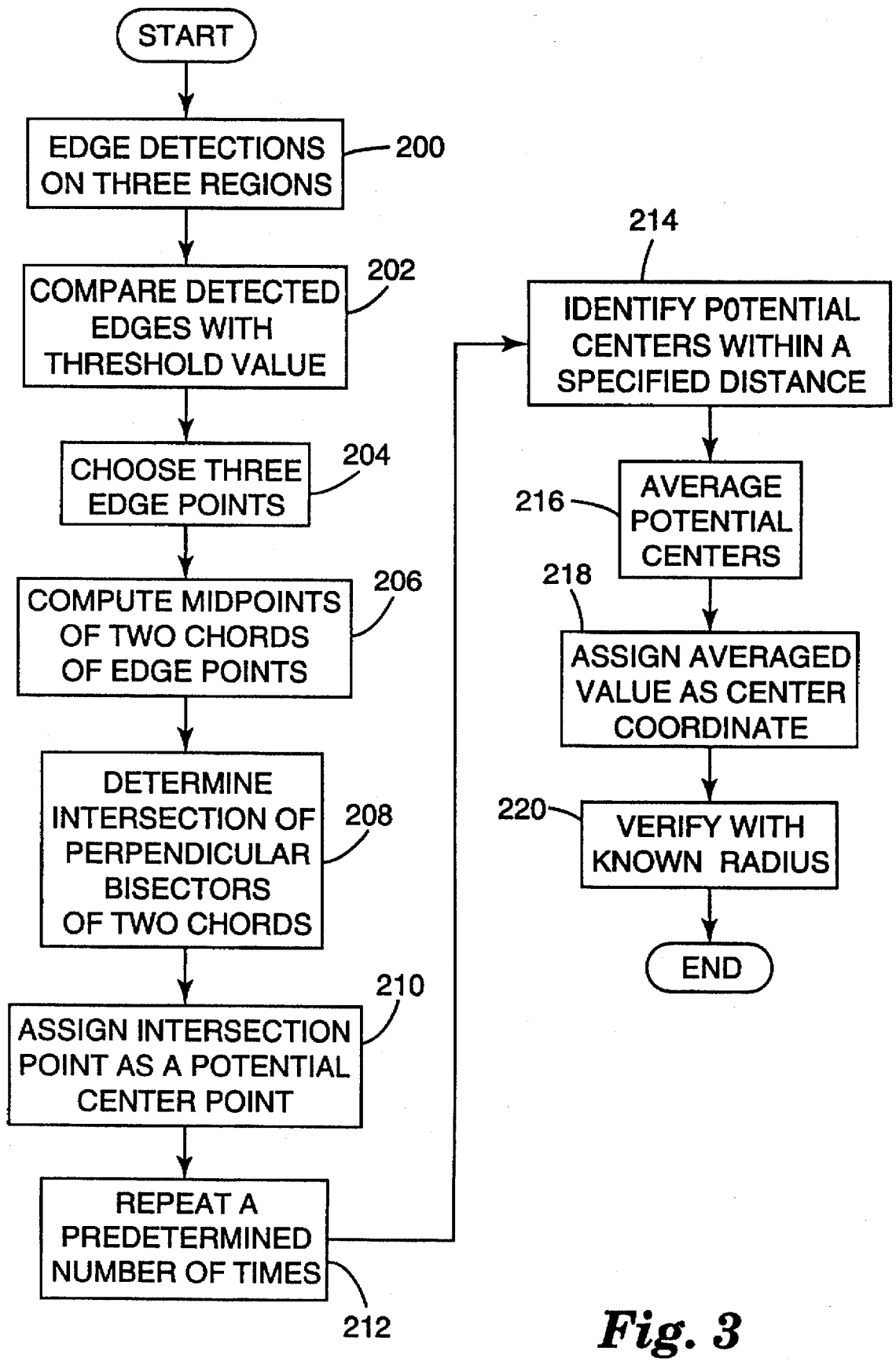
FIG. 3 is a flow diagram of a preferred method of determining the center of a circular growth medium.
Figure 4:
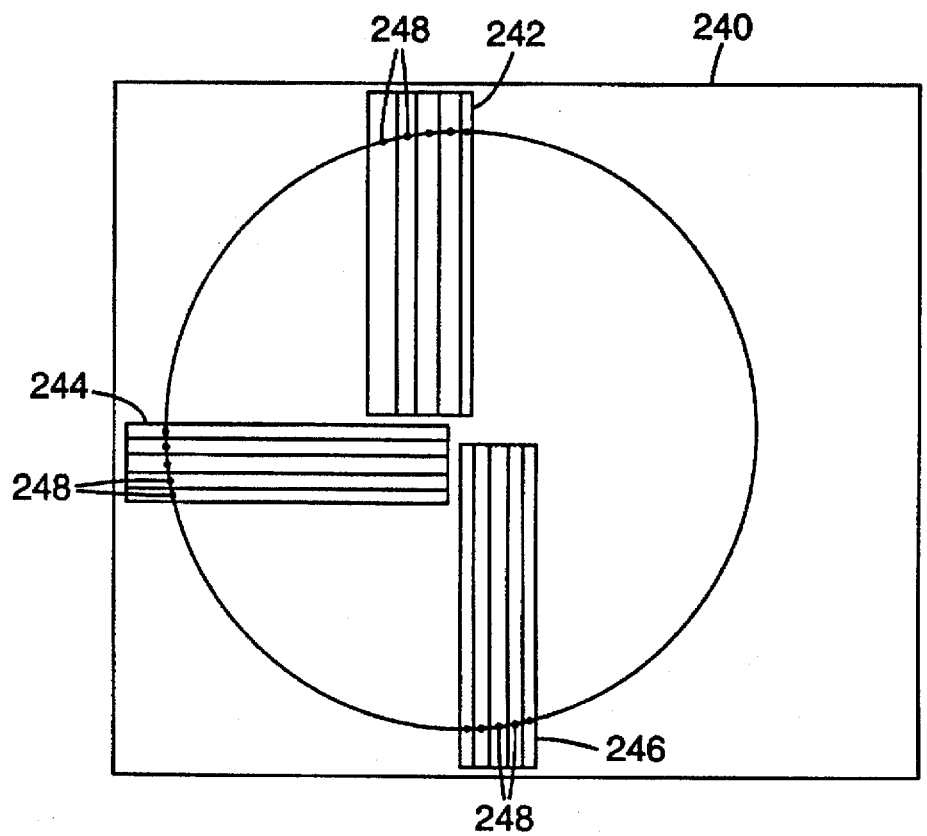
FIG. 4 shows how three regions are applied to a circular growth medium to determine edge points on the growth medium.

Referring to FIG. 3, a preferred method of locating the center of the circular gelatinous media of culture plate 32 is shown. The method shown in FIG. 3 assumes that the diameter of all culture plates is a known constant. At block 200, edge detection is performed on three regions of the image. The edge detection is performed to identify points located on the edge of the circular media. Edge detection is preferably performed in three regions by applying three edge detection kernels to the regions. The regions are strategically chosen such that the edge of the circular media will pass through each region. In FIG. 4, a preferred embodiment is shown wherein regions 242, 244 and 246 extend from near the center of image 240 to the edge of image 240. The width of the regions may vary, depending on the resolution of the system, the size of the growth medium and the optical system used to collect the image. Regions 242, 244 and 246 preferably lie at right angles to each other as shown in FIG. 4. In a preferred embodiment, a horizontal edge detection kernel is applied to pixel columns within regions 242 and 246 while a vertical edge detection kernel is applied to pixel rows within region 244 to obtain sets of three potential edge points, such as the three potential edge points in set 248. Several sets of potential edge points are obtained to produce three arcs along the edge of the circular media. Preferably, five sets of potential edge points are obtained. At block 202 in FIG. 3, the potential edge points are compared with a predetermined threshold value indicating that the potential edge points exceed a minimum level representing the likelihood that a potential edge point is located on an edge and thus are likely edge points rather than, for example, defects in the media. Potential edge points that exceed the threshold value are designated as edge points.

Figure 5:
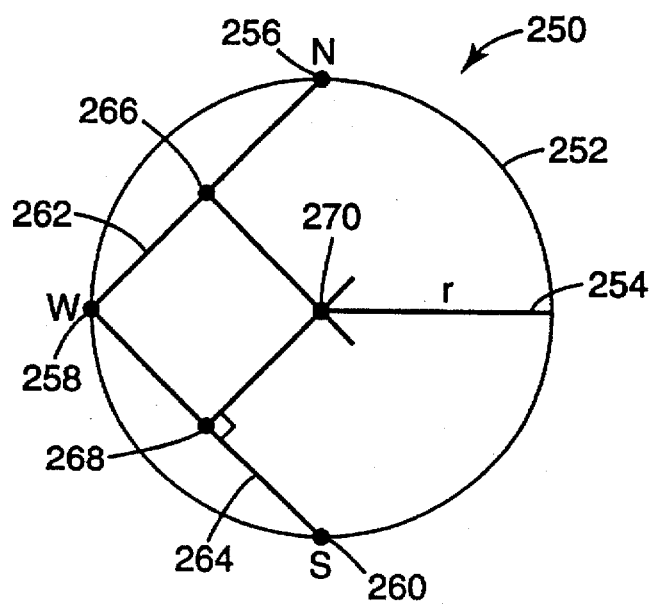
FIG. 5 shows how the center of a circular growth medium is determined after three edge points have been identified.

At block 204 of FIG. 3, a set of three edge points are chosen to determine the center of the circular media. Referring to FIG. 5, circular media 250 has circular edge 252 and radius, r, 254. The set of edge points consists of edge points 256, 258 and 260, designated N, W and S, respectively. At block 206, the midpoint of chord 262 between edge points 256 and 258 and the midpoint of chord 264 between edge points 258 and 260 are determined. The negative reciprocal of the slopes of chord 262 and 264 are used to obtain the slopes of the perpendicular lines to each of the chords, and the perpendicular lines are placed at midpoints 266 and 268 to form perpendicular bisectors of the two chords. At block 210, potential center point 270 of circular media 250 is then determined by locating the intersection point of the perpendicular bisectors of chords 262 and 264.

Figure 6:
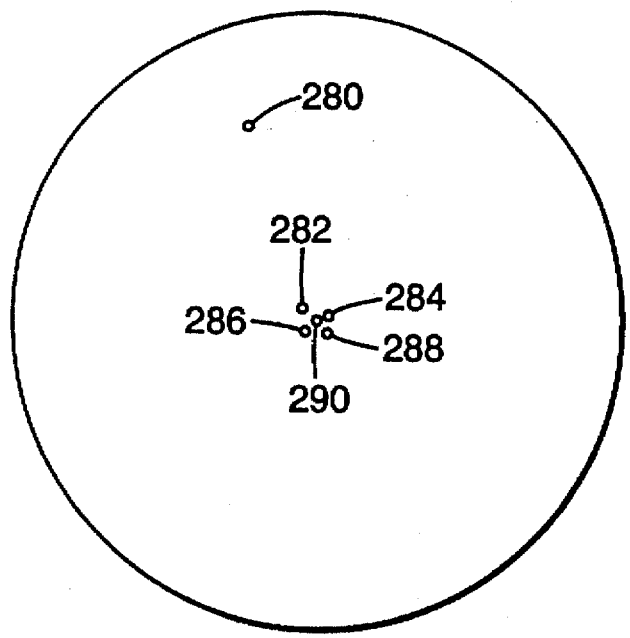
FIG. 6 shows how the center of a circular growth medium is determined after a plurality of potential center points have been determined.

At block 212, the process of selecting another set of three edge points and determining a potential center point is repeated a predetermined number of times. Once a set of potential center points is determined, the set is examined to identify one potential center point that has a predetermined number of potential center points within a specified distance of it. The center coordinate that meets this criteria is averaged with the other center coordinates that were within the specified distance at block 216 to obtain a final center coordinate at block 218. For example, referring to FIG. 6, five potential center points, 280, 282, 284, 286, and 288 are obtained from five sets of edge points. If the predetermined number of potential center points is three and if the maximum distance that each potential center point must be within is ten pixels, then potential center points 282, 284, 286 and 288 are averaged to determine final center coordinate 290. This method eliminates centers identified using faulty edge points, such as potential center point 280.

At block 220, a further verification of the final center coordinate may be performed in certain circumstances. If the circular media radius is known, the distance from the final center coordinate to any edge point may be compared to the known radius to ensure the distances are close in value.

The final center coordinate defining the center of the circular media may be used in many ways. For example, it is possible to have false detections of colonies outside of the circular media due to the rapid media dehydration that typically occurs at the edges. Thus, at block 104, the center coordinate may be used when applying a mask to the image to ensure detection of microbial colonies is not performed outside the media. The mask can be centered at the computed center coordinate, allowing both fast and accurate application of the mask to the image. Further, when carrier 30 is used as shown in FIG. 1, a mechanical system is typically included to provide repeatable positioning of carrier 30 such that a plurality of culture plates 32 may be monitored by system 10. Mechanical systems by their nature, however, can occasionally produce translational error. By identifying the center of the circular media of the culture plate, the system can compensate for possible translational error at block 106. The identified center can be used as a reference point such that successive images are aligned. The limited processing necessary to ascertain the center of the growth media using the preferred method is faster than prior art methods of determining the center. Thus, the center of the growth media can be determined for every image using the method of the present invention, thereby increasing the accuracy of the processing because translational error can be corrected for every image.

In a preferred embodiment of the present invention, time lapse subtraction is performed to create a difference image. As will later be described, however, time lapse subtraction is not necessary with some culture plates and detection and identification of microbial colonies can be performed with only a final image. Time lapse subtraction uses a pair of images of the growth medium from different times and processes the two images to produce a difference image. The difference image is the resulting image from taking the difference between the two images. The difference image aids in early detection of microbial colonies because small color changes are easily detected, and therefore has an improved signal-to-noise ratio compared to either of the unprocessed images alone. Further, analyzing unprocessed images alone can result in voids and color variations in the growth media being mistaken as colonies. The subtraction effectively eliminates this problem.

After the initial acquired colony image has been registered and stored to memory, culture plate 32 is incubated for a predetermined period at block 110. In culture plates where time lapse subtraction is preferably performed, such as with PETRIFILM P2000 Coliform Culture Plates, subsequent images are acquired in predetermined incubation intervals and difference images are acquired at block 112. A first colony image is collected at block 100. To collect this image, a green band pass filter 24 is placed in front of lens 22 of camera 20. The green filter preferably has a spectral peak at 550 nm and a bandwidth of 40 nm. The green filter is sensitive to the yellow color produced by microbial colonies growing on the preferred culturing devices 32. The first colony image is preferably collected after an initial incubation period. For example, for a PETRIFILM P2000 plate, a first image is preferably collected approximately three hours after incubation, as detectable growth typically occurs after approximately four hours. Using the center coordinates of the growth medium as determined at block 102, the growth medium is registered by translating it to a reference position in the image. The registered first colony image is stored in memory 14, such as a hard disk on a personal computer. The culturing device is incubated for a predetermined time interval, such as one hour, at block 110 and a second colony image is collected at block 100. The second colony image is also collected using the green filter. The predetermined time interval for incubation may vary based on the growth rate of microbial colonies being detected, and the sensitivity of imaging system 10. The predetermined time interval further is dependent on the indicia of colony growth, for example, the sensitivity of the pH indicator and the pH of the inoculant. The second image is also registered to the reference position in the image at block 106.

At block 112, a difference image is computed. The registered first colony image pixels are subtracted from corresponding pixels in the registered second colony image. The resulting values from the pixel-by-pixel subtraction are assigned to corresponding pixels in the difference image. Thus, the difference image represents the difference in intensity for corresponding pixels in the first and second colony images collected at successive time intervals. When the system encounters the first colony image at block 108, it incubates the growth medium for the predetermined incubation period because two images in sequential time periods are necessary to obtain a difference image. In subsequent iterations of computing difference images, however, only the second colony image for the iteration is collected. The second colony image from the previous iteration is used as the first colony image in the subsequent iteration. Therefore, it is only necessary to store to memory the single colony image from the previous time period for each growth medium.

Figure 7A:
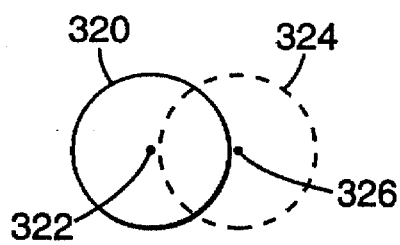
FIG. 7a shows two close colonies.
Figure 7B:
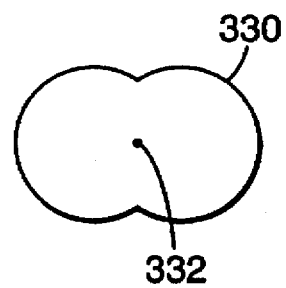
FIG. 7b shows how prior art methods and apparatuses might determine that the two close colonies of FIG. 7a are a single colony.

Once a difference image has been computed, processor 12 processes the difference image data to identify potential colonies. When culture plate 32 is incubated, microbial colonies on the growth medium produce acid. When acid is produced by each microbial colony, the acid spreads out relatively evenly in all directions from the point of origin of the colony, a central peak. In general, the more acid produced by a colony, the larger the diameter of the circle surrounding the central peak of the colony. Typically, the difference in intensity at the central peak of the colony between subsequent colony images is greater when more acid is produced, and is indicated in the difference image. Processor 12 models each potential colony based on the general tendencies of colonies to grow from a central peak and in a circular fashion. Processor 12 then can track the formation and growth of the acid zones around the central peaks to make more informed decisions when contemplating the detection of new colonies. The modeling of each colony allows system 10 to differentiate between close colonies as well as assists in determining whether a detected potential colony is merely noise produced by previously identified colonies or is dust, food particles or voids in the media. For example, FIG. 7a shows two close colonies, first colony 320 with first central peak 322 and second colony 324 with second central peak 326. The present method and apparatus can differentiate the two close colonies. Some prior art systems, however, might identify the two close colonies shown in FIG. 7a as a single colony 330 with a single central peak 332 as shown in FIG. 7b. The modeling of colonies therefore allows system 10 to more accurately detect and locate microbial colonies. While the preferred method and system use acid as a growth indicator, those skilled in the art will readily recognize that indicia of colony growth other than acid may be analyzed to monitor colony growth.

Referring back to FIG. 2, the processor determines if the difference image is the first difference image encountered for the growth medium at block 114. Before searching for new colonies in a difference image, processor 12 typically will first monitor and track the growth of existing colonies, as will later be described. When processor 12 encounters the first difference image for a growth medium, however, it is unnecessary to monitor the growth of existing colonies because none exist. Under such circumstances, the difference image acquired by time lapse subtraction is immediately processed by processor 12 to detect central peaks in the image at block 118, thereby bypassing the step of tracking the growth of existing colonies at block 116.

Figure 8:
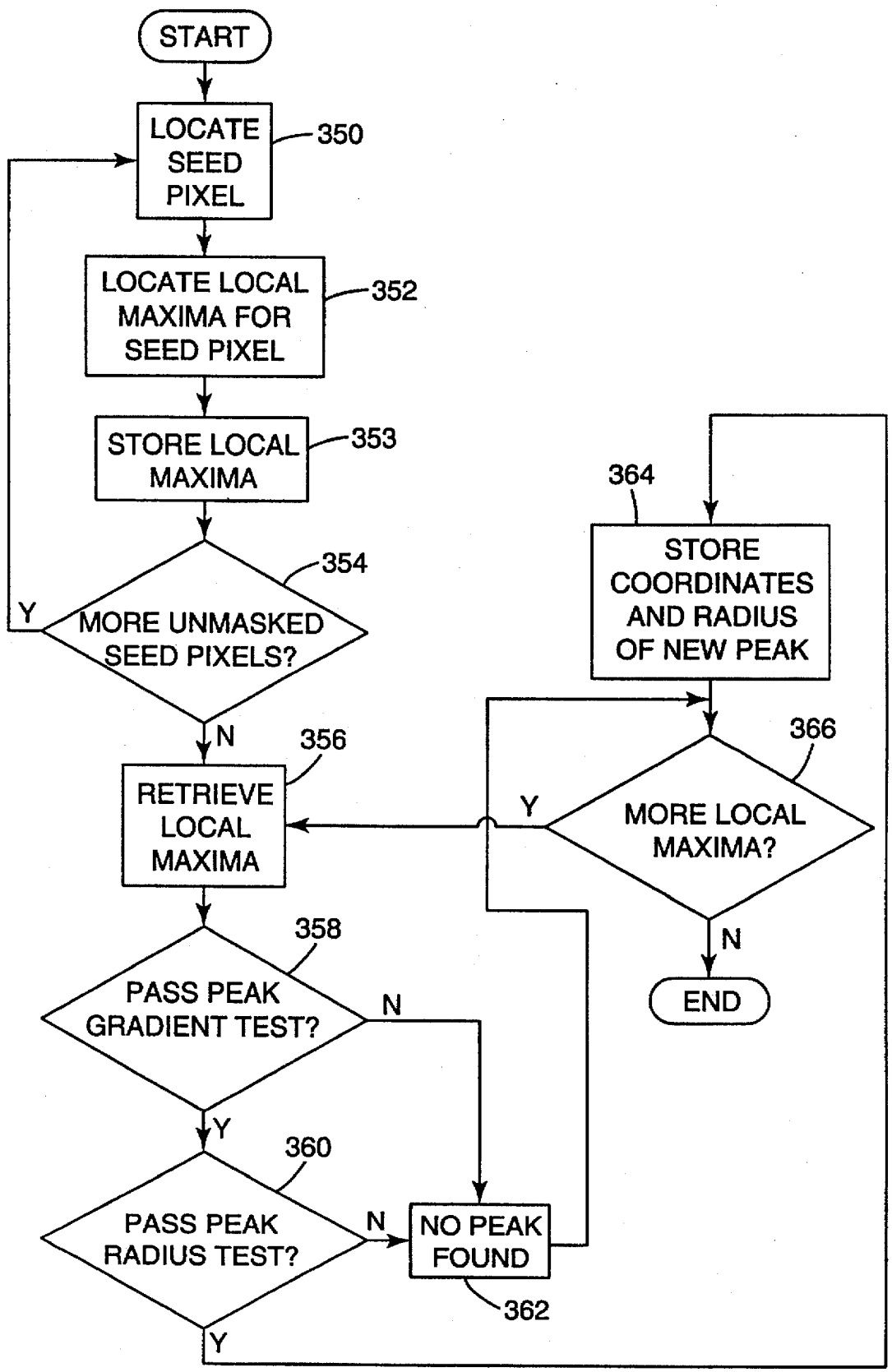
FIG. 8 is a flow diagram of a preferred method of finding peaks in a difference image.

FIG. 8 shows a preferred method of new peak detection. After an initial recovery period, the colony becomes a point source of acid production. The acid spreads due to diffusion in the growth media. FIG. 9 shows a grid of numbers representing a portion of a difference image for a regions of the growth medium where an acid spot is forming. The numbers shown in FIG. 9, difference intensity values, represent the magnitude of change in color intensity between a first image and a subsequent second image obtained after a predetermined incubation period. A value of zero represents no change. Acid produced in a microbial colony typically has a peak difference in intensities of between four and 40. In FIG. 9, the peak value, shown in bold, is eight. The difference in intensities between two time lapsed images appears in the difference image as a gaussian distribution. Thus, the peak value occurs near or at the center of the acid zone and dissipates gradually outward in all directions, as can be seen by the numbers decreasing in value surrounding the peak value of eight in FIG. 9. The method shown in FIG. 8 locates the central peaks and further analyzes the pixels surrounding the central peaks to detect and identify potential microbial colonies.

Figure 10:
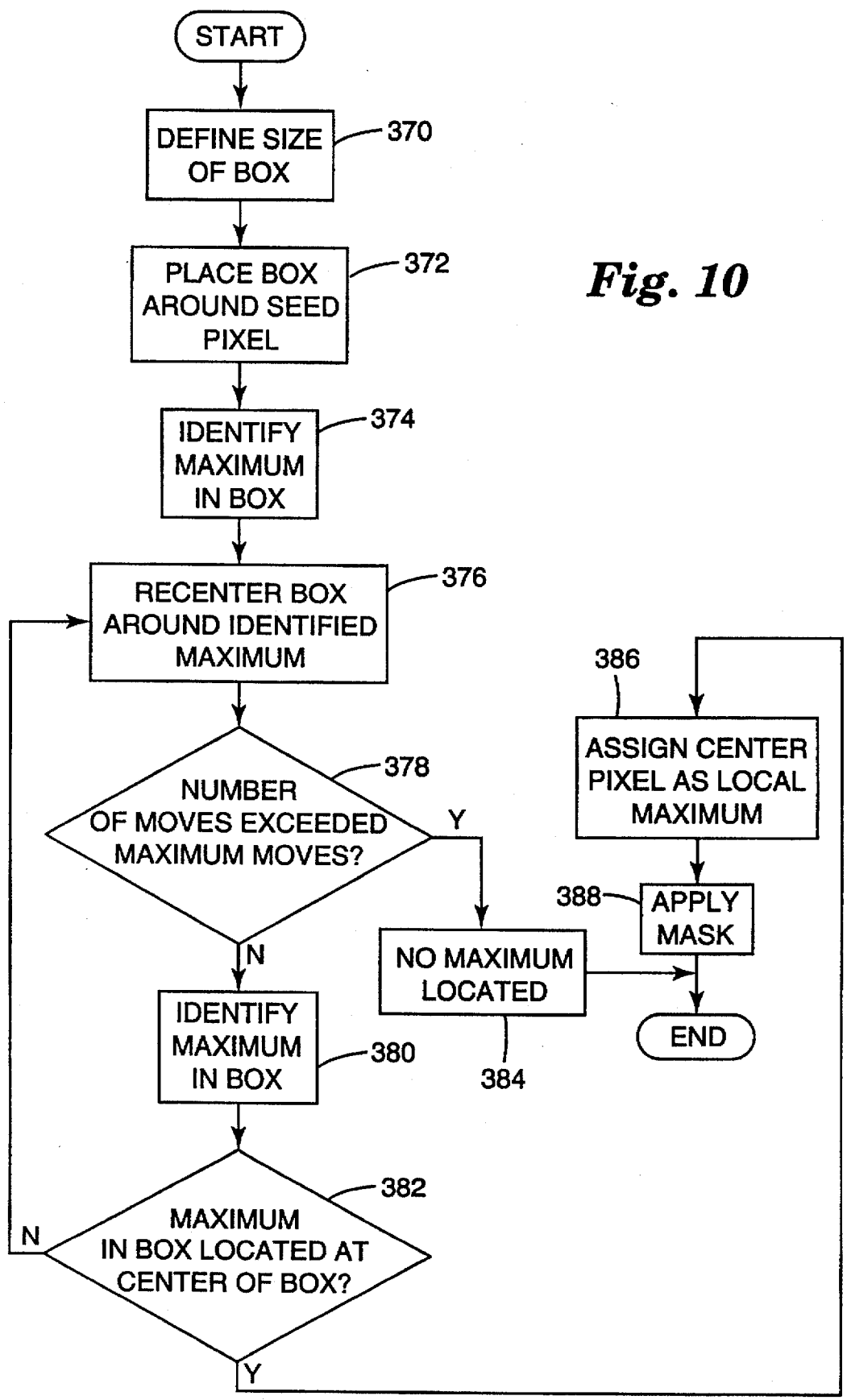
FIG. 10 is a flow diagram of a preferred method of determining local maxima associated with seed pixels.

At block 350 of FIG. 8, a first seed pixel is located by processor 12. Seed pixels are pixels that have a difference intensity value greater than or equal to a minimum threshold value. To identify seed pixels, non-masked areas of the difference image are scanned pixel-by-pixel, such as from left to right and top to bottom. For example, in FIG. 9, if the minimum threshold value for seed pixels was four, seed pixel 400, with a difference intensity value of four, would be the first pixel satisfying the criteria to be a seed pixel. Once a seed pixel is located, a local maximum for the seed pixel is located at block 352. A preferred method of determining the local maximum for a seed pixel is shown in FIG. 10. The method shown in FIG. 10 attempts to find local maxima associated with a seed pixel, or peaks in the image, as quickly as possible. The size of a box used to determine the local maximum is defined at block 370. The size of the box is chosen such that colonies that are close together can be distinguished. Thus, the size is dependent on the resolution of the system and experimental data, such that only one colony peak will fit inside the box when centered in the box. In FIG. 11, a box size of five is chosen, such that box 410 is a five pixel-by-five pixel box. At block 372, the box is placed around the identified seed pixel. In a preferred embodiment, the seed pixel is centered in the top row of pixels in the box. For example, in FIG. 11, seed pixel 400 is centered in the first row of box 410. After the box is placed around the seed pixel, a maximum difference value within the box is identified at block 374. Each pixel within the box is scanned to determine the pixel or pixels with the largest value. If there are several pixels with a common largest value, a centroid of the common pixels is computed and assigned as the location of the maximum difference value. Referring back to FIG. 11, the maximum difference value within box 410 is pixel 402 with a value of seven. Once the location of the maximum difference value is identified, the box is centered around that location. In FIG. 11, box 410' is moved and centered around pixel 402.

Once the box has been centered around the maximum difference value, the steps of identifying the maximum difference value within the box and recentering the box around the new maximum difference value are repeated in blocks 380 and 376. These steps are repeated until either a maximum number of box moves exceeds a predetermined maximum number of moves, signaling that no peak could be identified for the initial seed pixel, or the maximum difference value is located at the center of the box, thereby signaling that a peak value has been identified. If the number of moves exceeds the maximum at block 378, processor 12 determines no maximum has been located at block 384. When the maximum value is located at the center of the box, the center pixel is assigned as the local maximum for the initial seed pixel at block 386. For example, in FIG. 11, the second box move would recenter box 410' around pixel 404 having a difference value of eight. Assuming the predetermined maximum number of moves is not exceeded, after the second move, pixel 404 having a value of eight is located in the center of the box and is the local maximum for seed pixel 400.

Each time a local maximum, or peak, is identified for a seed pixel, a circular mask having a predetermined radius is applied to the difference image at block 388. The radius of the mask is based on the resolution of system 10, and more specifically, camera 20. Once the resolution is known, the mask radius is preferably set to equal the radius of the smallest detectable colony of the imaging system. For example, if the resolution of the system is 0.1 mm per pixel, and the smallest detectable colony has a radius of 0.5 mm, then the mask radius would preferably be at least 5 pixels. The mask is centered at the local maximum and eliminates the possibility of redundant detection of the peak and increases the speed of detecting and identifying peaks within the difference image. Referring back to FIG. 8, the local maximum for the seed pixel is stored at block 353. At block 354, the process of locating seed pixels and their corresponding local maxima is repeated until no more unmasked seed pixels exist.

Figure 12A:
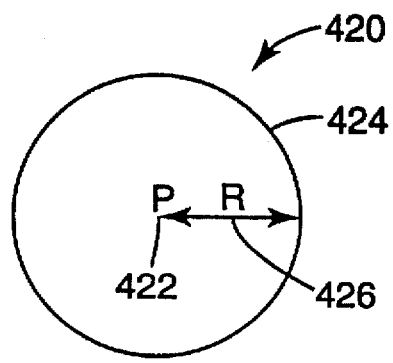
FIG. 12a and 12b show top and side cross-sectional views of a modeled microbial colony.
Figure 12B:
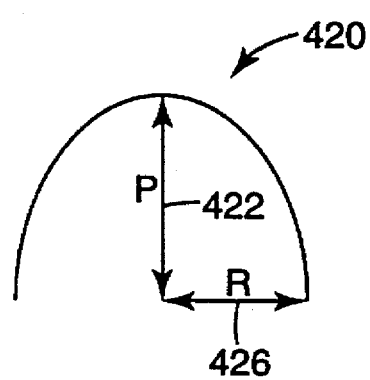

Once all local maxima are identified and stored, each local maximum must be qualified by passing both a peak gradient test and a radius test, to later be described, before being added to a list of potential new colonies. The qualification of each local maximum utilizes a model of the acid zone that spreads and surrounds each colony peak as shown in FIGS. 12a and 12b. Acid produced at the peak typically spreads in a circular fashion. FIG. 12a shows a top view of colony model 420, where acid is produced at peak, P, 422 and spreads to colony edge 424, forming a circle having radius, R, 426. FIG. 12b shows a side cross-sectional view of colony model 420, having peak 422, which represents the difference intensity value, and radius 426.

Referring to FIG. 8, a local maximum representing a potential new colony is retrieved from memory at block 356. This local maximum is first subjected to a peak gradient test at block 358, which indicates whether a gradient from the peak decreases in a predetermined number of directions, or as ideally occurs, in all directions as shown in the cross-sectional view of colony model 422. Preferably, the gradient test examines the pixel values in eight directions, such as the eight compass directions shown in the bold pixel values in FIG. 13. In each direction, the pixels are examined outward from the peak to determine if the values of the pixels decrease over a predetermined minimum gradient distance, such as three pixel lengths. To pass the gradient test, the pixels values must decrease over the minimum gradient distance in at least a predetermined number of directions, such as six directions. Further, if the intensity value for any pixel in a particular direction is below a minimum intensity value, indicating the pixel is in the background zone, then the test fails for that direction.

For example, in FIG. 13, assuming the maximum intensity value indicating a background pixel is two, the intensity values decrease over a distance of three pixels in the east, south and west directions. In the northeast, southeast and southwest directions, the intensity values decrease over a distance of 2.83 pixel lengths and in the northwest direction, the intensity values decrease over a distance of 5.66 pixel lengths. In north direction 430, however, after decreasing from eight to five, the intensity value increases to six. Assuming the predetermined minimum gradient distance is two pixel lengths, the gradient test would fail in this direction. Therefore, the gradient decreases in seven of the eight directions, and the local maximum would pass the gradient test if the predetermined number of distances required is seven or less. If the local maximum fails the gradient test, no peak is found at block 362 and the process is repeated for the next local maximum at block 366.

If the local maximum passes the gradient test, it is deemed to have a peak and the colony is assumed to be generally circular. Thus, the radius test is performed on all peaks which have passed the gradient test to determine the radius of the circle at block 360. In a preferred method of determining the radius, pixel values in each direction of the eight compass directions, are scanned, starting from peak under examination, until one of three conditions are met.

The first condition is met if the length of the radius exceeds a maximum radius. This maximum is based on prior experience with colony growth and is set to the maximum number of pixels that acid can spread in a predetermined period. Thus, if the computed radius reaches the maximum allowable radius, the radius is set equal to the maximum allowable radius. This condition identifies situations as shown in FIG. 14, where five colonies are growing in close proximity, and the radius for peak 430 may be incorrectly determined to be radius 432, if that length exceeds the maximum number of pixels. If the radius is incorrectly set to the maximum pixel length, the error is accounted for later in the peak radius test.

The second condition is met when the next pixel value is less than the a predetermined minimum intensity value, indicating the pixel is in the background. Theoretically, background is indicated by a difference intensity value of zero. In practice, however, noise requires a value greater than zero, such as three, for the minimum intensity value. When this condition is met, the radius for the peak is set to the number of pixel lengths from the peak pixel to the minimum intensity pixel.

The third condition is met when a subsequent pixel value exceeds the immediately previous pixel value by more than a predetermined noise value. This predetermined noise value allows for noise as well as for closely growing colonies. For example, this noise value may be between zero and three depending on the microorganism. FIG. 15a and 15b demonstrates how the noise value differentiates between the two situations. In FIG. 15a, two colonies, colonies 440 and 442 are growing in close proximity. Colony 442 has peak 444 and a radius 446 in a first direction. In another direction, however, the acid produced by peak 444 of colony 442 spreads into the acid produced by peak 440. In such a direction, at overlapping point 450, the intensity values begin to increase and exceed the predetermined noise value. In this direction, colony 442 correctly has a radius of 448. In FIG. 15b, colony 460 correctly has a radius of 462. If the noise value is set too low, however, an incorrect radius value may be obtained. In FIG. 15b, at location 466, noise, possibly caused by some defect in the media such as a food particle or other foreign particle, results in additional acid being produced and a larger difference intensity value at 466. If the noise value is set at zero, for example, incorrect radius 464 will be obtained when the pixel intensity value at 466 exceeds the noise value. If the noise value is set at an appropriate value, however, the noise at 466 will not exceed the noise value and radius 462 will correctly be obtained when the second condition is met.

After a radius length has been determined for all directions, a colony radius is computed. In a preferred embodiment, the colony radius is the median of all measured radii. While a simple average may also be used, it is preferable to compute a median to avoid the weighted effects of incorrect radii lengths at either extreme, such as an incorrect maximum radius length obtained in the first condition. While a median is preferred, any method of determining a median-type value is contemplated by the present invention. For example, the middle values from the measured radius values may be averaged. The computed colony radius is compared with a minimum radius, determined experimentally based on the smallest detectable colony, such as 2.1 pixel lengths, and the peak radius test passes if the computed colony radius is greater than the minimum radius. If the computed colony radius is less than the minimum radius, the peak radius test fails and no peak is found for the local maximum at block 362 and the process is repeated for the next local maximum at block 366.

Figure 16:
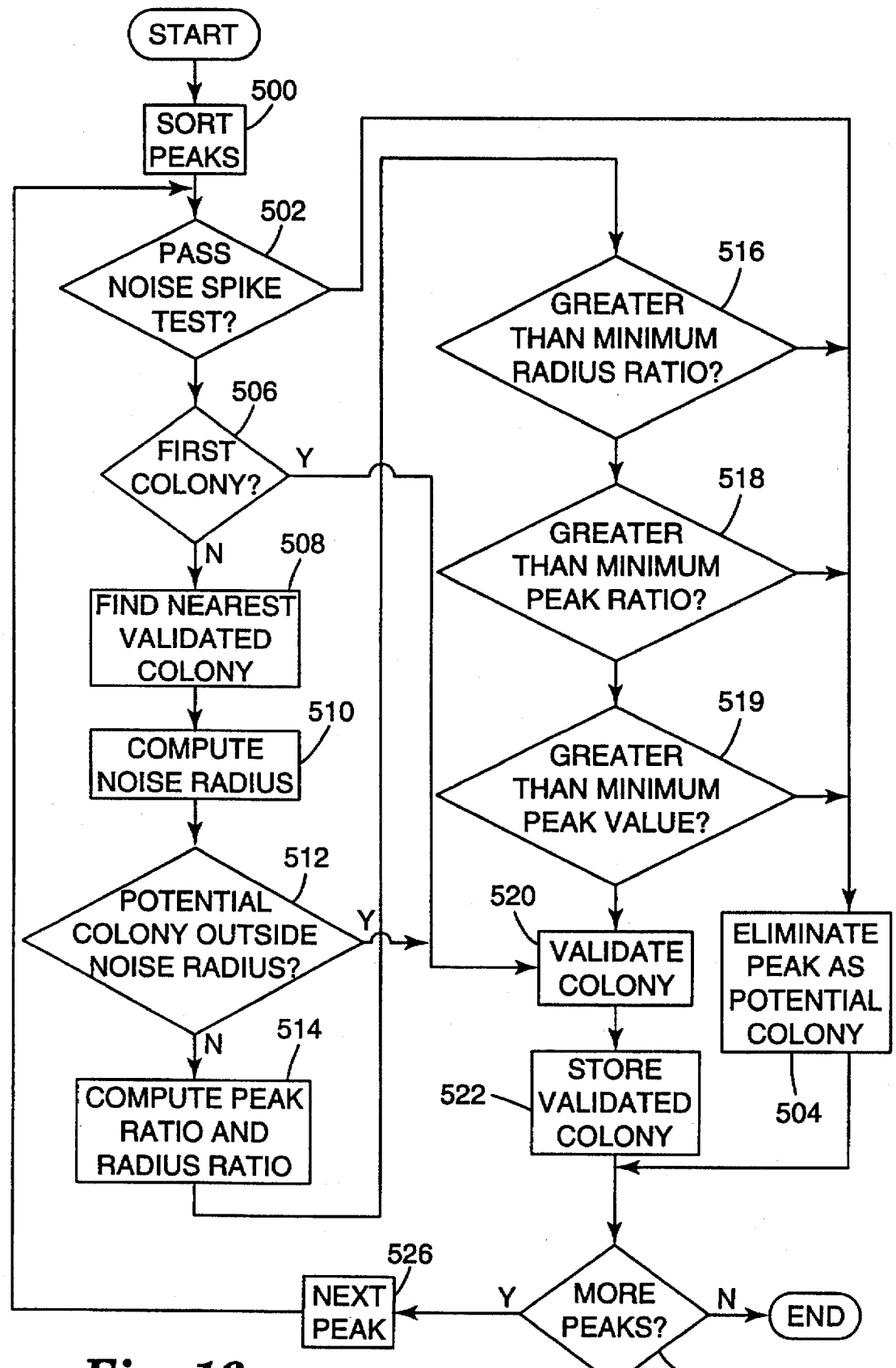
FIG. 16 is a flow diagram of a preferred method of validating potential colonies.

If a local maximum passes both the peak gradient test at block 358 and the peak radius test at block 360, the difference intensity value of the peak, its coordinates and its corresponding radius are stored to memory as a potential colony at block 364 of FIG. 8. The peaks stored to memory, which represent potential colonies, are then analyzed at block 120 of FIG. 2 to validate that the peaks are truly colonies rather than a void or dust which look like acid produced by a microbial colony. Peak validation further facilitates detection of significant acid zones surrounding peaks and reduces the chances of falsely identifying a weak peak that is merely noise in the outer acid zone of a larger colony as a new colony. FIG. 16 shows a preferred method of validating colonies. Peaks are sorted according to their peak values at block 500 such that the highest peaks, the peaks with the largest difference intensity values at the center of the circular colony, are at the beginning of the potential colony list and the lowest peaks, the ones with the smallest difference intensity values at the center of the circular colony, are at the end of the list. FIG. 17 shows an example of a portion of a list of detected potential colonies sorted in order of their peak values.

The next step in validating the potential colony is determining whether the peak value is due to dust, a void in the growth medium or other foreign particle. Difference images typically indicate these artifacts as very bright, thin regions of activity. FIG. 18 graphically shows an example of a cross-section of dust. Translated into numerical criteria, the dust will have a very large peak value and die off abruptly, such as Peak Number 1 in FIG. 17. Thus, the dust will also have a relatively small radius with respect to the large peak value. At block 502, a ratio of the peak value to radius is determined and compared with a noise ratio. If the ratio of peak 550 to radius 552 of dust 554 exceeds the noise ratio, then the peak is considered a noise spike and eliminated. The noise ratio is dependent on the growth medium, as acid produced by microbial colonies is more viscous on some growth media than others. For example, for a noise ratio of five, when the peak value is more than five times as great as the radius value, the peak is considered a noise spike. Peak Number 1 in FIG. 17 is over twelve times as great as the radius, would fail the noise spike test at block 502 of FIG. 16 and would be eliminated from the potential colony list at block 504. Alternatively, rather than using a ratio, peak and radius values can be compared to a maximum peak value and a minimum radius value. In this approach, if both a peak value is greater than a maximum noise peak value, such as 20, and its radius is less than a minimum noise radius value, such as four, the peak can be disqualified as a potential colony. While in the preferred embodiment, ratios are calculated, those skilled in the art will readily recognize that functions other than ratios can be derived from the peak values and radius values to determine if the peak is considered a noise spike.

If the peak subjected to the noise spike test is the first peak to pass the test for the growth medium at block 504, then the peak is officially confirmed as a new colony, or validated, at block 520, and stored as a validated colony at block 522. For all subsequent peaks, after passing the noise spike test, the peaks are further analyzed to determine if they are noise on the outer acid zone of a larger peak. FIG. 19 shows a model colony 560 having radius 562 and actual colony 564. In the peak radius test, colonies are modeled as a circle although in reality, they are merely generally circular. Therefore, acid produced at the peak of the colony will typically exist outside the median radius of the model colony. Further, at the edges of the acid zone, non-uniform growth can appear as noise. This noise may be due to defects in the growth medium, thereby causing slower acid growth, or foreign particles in the media that may change the rate of acid production. On the periphery of the acid zones, peaks often occur that are not caused by microbial colonies and should not be counted.

At block 508, the distance from the potential colony to the closest validated colony is computed. FIG. 20 shows potential colony 540 and validated colony 542. The validated colony closest to potential colony 540 is the validated colony having an edge closest to the edge of potential colony 540, where distance, X, 544 between the edges is a minimum.

Figure 21B:
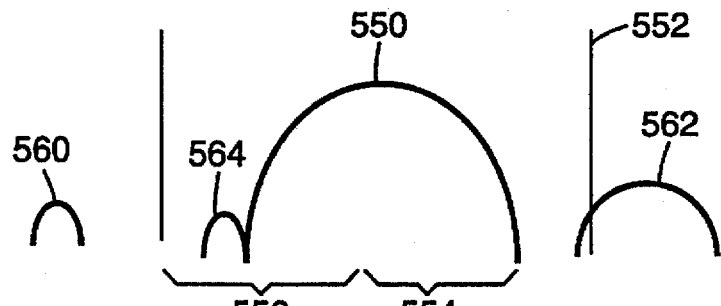

Once the closest validated colony to the potential colony is identified, a noise radius is computed for the validated colony at block 510. The noise radius forms a concentric circle with the edge of the validated colony and surrounds the validated colony. FIG. 21*a* shows top view and FIG. 21*b* shows a side cross-sectional view of noise-circle 552 around validated colony 550. Noise radius 556 is a fraction larger than colony radius 554 to take into account the imperfections of the colony model as earlier described and shown in FIG. 19. For example, in FIGS. 21*a* and 21*b*, noise radius 554 is 0.7 times larger than validated colony radius 556. The length of the noise radius will vary depending on the growth media. Further, if the noise radius is less than a minimum noise radius, the noise radius is set equal to the minimum noise radius.

Once the noise radius had been computed, the location of the potential colony is compared to the noise circle defined by the noise radius. If the potential colony lies completely outside the noise circle at block 512, it is confirmed as a validated colony at block 520 and stored at block 522. Referring to FIGS. 21*a* and 21*b*, potential colony 560 is an example of a potential colony that lies completely outside noise circle 552.

If the potential colony does not lie completely outside the noise circle at block 512, additional analysis is required to distinguish whether the potential colony is truly a new colony or whether it is noise produced by the closest validated colony. At block 514, a ratio of the peak values and a ratio of the radius values of the potential colony and the validated colony are computed. While ratios are used in the preferred embodiment, those skilled in the art will recognize that many values derived from the relationship between peak pixel values and colony radius values may also be used. The center peak value used for the validated colony is the maximum center peak value observed over its lifetime. The radius ratio is compared to a minimum radius ratio, such as 0.33. If the radius ratio is less than the minimum radius ratio at block 516, then the potential colony is determined to be noise and eliminated at block 504. If the potential colony passes the radius ratio test, then the peak ratio is compared to a minimum peak ratio, such as 0.5. If the peak ratio is less than the minimum peak ratio at block 518, the potential colony is eliminated at block 504. Finally, at block 519, the center peak value of the potential colony is compared to a minimum peak value. If the center peak value is less than the minimum peak value, the potential colony is eliminated at block 504. If the potential colony passes the radius ratio test, the peak ratio test and the peak value test, the potential colony is confirmed as a validated colony at 520 and stored at block 522. The radius ratio, peak ratio and peak value will vary depending on the growth media, imaging system resolution and dynamic range. A minimum radius value may also be required to confirm a potential colony as a validated colony. Referring back to FIGS. 21*a* and 21*b*, potential colony 562 is an example of a colony that would pass the three tests and be confirmed as a validated colony while potential colony 564 would fail at least two of the three tests and be eliminated. At blocks 524 and 526, the process is repeated for all remaining potential peaks, each time analyzing the potential colony with the largest remaining peak value.

Referring to block 114 of FIG. 2, if the difference image is not the first difference image, and existing colonies have been identified in previous difference images, the growth of previously identified validated colonies is monitored at block 116. The validated colonies are examined and their current peak value is compared with the past maximum peak value for the colony. The maximum peak value for each validated colony is stored for use in computing the peak ratio when validating potential colonies, as was earlier described. Therefore, if the current peak value is greater than the past maximum peak value, the current value is stored to memory in place of the past maximum peak value. The radius of the validated colony is also updated. Radius measurements begin from the edge of the previously identified colony and proceed outward in the same predetermined number of directions, such as the eight compass direction. Finally, the pixels comprising the updated validated colony are masked off to eliminate unnecessary processing on portions of the image that have already been identified as colonies.

After peaks have been validated, the validated colony data may be analyzed at block 122 and output at 124, if desired. Many types of analysis are possible with the data associated with the validated colonies. For example, the number of validated colonies can be counted at each time interval to provide colony count information. The early initial detection of the colonies coupled with the subsequent tracking of the growth of the colonies over the remainder of the incubation time allows the system to detect and enumerate growing microbial colonies at the earliest possible time. This early enumeration can provide presumptive counts before the expiration of the incubation period. For example, when 3M brand P2000 Coliform Count Plate is used as a growth medium, a preliminary count may be provided as early as five hours after incubation has commenced with a final presumptive count provided at fourteen hours. A confirmed count cannot be provided until 24 hours. Other types of data may be output at block 124, such as the location of colonies, their size and their rate of growth.

After analysis of the difference image is complete for the time period, the growth medium is incubated for the predetermined incubation period at block 110 unless the incubation period, such as 24 hours, has expired at block 126. After the incubation period has expired, a confirmed count of the colonies may be provided.

Figure 22:
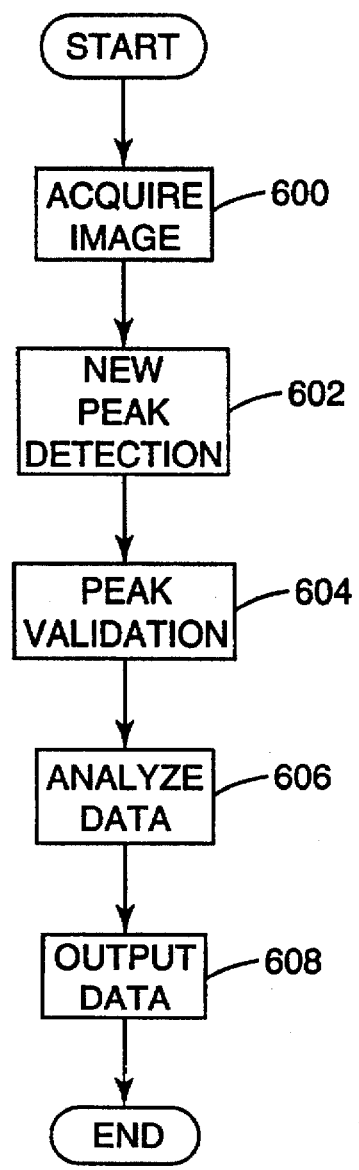
FIG. 22 is a flow diagram of a method of detecting and identifying microbial colonies when a difference image is not computed.

While a method has been described for providing presumptive colony counts before expiration of the incubation period by utilizing difference images from sequential images, a confirmed count can also be provided using a similar method, without time lapse subtraction, for selected growth media. An example of such a selected growth medium containing an oxidation reduction indicator, triphenyltetrazolium chloride (TTC), is 3M brand PETRIFILM Aerobic Count Plate (AC Plate). Such a growth medium may be used with or without time lapse subtraction because color changes that surround a growing microbial colony have a high contrast with respect to the growth medium, specifically a red colored area on a white/beige background. With such a growth medium, no difference image is required. Therefore, a single image of the growth medium is acquired after the incubation period has expired. Referring to FIG. 22, after an image is acquired at block 600, new peak detection is performed at block 602. Because the system will be analyzing an image of the growth medium rather than a difference image, the system analyzes the raw pixel intensities. For the AC Plate, the peaks are the red areas on the white background and will be the lowest intensity pixels in the image. Therefore, rather than searching for the maximum using the method in FIG. 10, the same method may be used to search for minimum pixel intensities. Alternatively, the negative of the image may be obtained and the maximum intensities may be determined. Then, similar to FIG. 8, the peak gradient test and the peak radius test are performed to identify the peaks and determine their radius.

At block 604, peak validation is performed. In one embodiment of the present invention, the method of FIG. 16 is used to validate the potential colony. In another embodiment, as peaks are located in block 602, they are stored as potential colonies and sorted based on the length of their radius. During peak validation, the colonies are validated from largest to smallest radius. The largest colony is automatically validated. For each potential colony thereafter, the nearest validated colony is first identified. The potential colony must be located a minimum distance from the nearest validated colony to be confirmed as a validated colony. If the potential colony is within the minimum distance, it is eliminated from the list of potential colonies and deemed to be noise. At blocks 606 and 608, the data associated with the validated colonies, such as number of validated colonies, their location, and their size may be determined and output.

Although a preferred embodiment has been illustrated and described for the present invention, it will be appreciated by those of ordinary skill in the art that any method or apparatus which is calculated to achieve this same purpose may be substituted for the specific configurations and steps shown. This application is intended to cover any adaptations or variations of the present invention. Therefore, it is manifestly intended that this invention be limited only by the appended claims and the equivalents thereof.

We claim:

1. A method for detecting and identifying microbial colonies in an inoculated growth medium, said method comprising the steps of:

a) imaging said growth medium to obtain first colony image data;

b) incubating said growth medium for a selected time interval;

c) imaging said growth medium to obtain second colony image data;

d) processing said first and second colony images to produce a difference image wherein said difference image is obtained by taking a difference between said first colony image data and said second colony image data;

e) identifying potential colonies within said difference image, each said potential colony having a peak pixel and a colony radius; and f) validating each said potential colony to ensure said potential colony is a validated colony by a method comprising the steps of:

i) eliminating said potential colony if said potential colony is a noise spike; and ii) eliminating said potential colony if said potential colony is noise around the perimeter of a validated colony.

2. The method for detecting and identifying microbial colonies according to claim 1, wherein said step of eliminating said potential colony if said potential colony is a noise spike comprises the steps of:

a) comparing a peak pixel intensity value of said peak pixel of said potential colony with a spike peak threshold value;

b) comparing said colony radius of said potential colony with a spike radius threshold value; and c) eliminating said potential colony if said peak pixel intensity value exceeds said spike peak threshold value and said colony radius does not exceed said spike radius threshold value.

3. The method for detecting and identifying microbial colonies according to claim 1, wherein said step of eliminating said potential colony if said potential colony is a noise spike comprises the steps of:

a) computing a computed value derived from said peak pixel intensity and said colony radius of said potential colony; and b) comparing said computed value to a spike peak value; and c) eliminating said potential colony if said computed value exceeds said spike peak value.

4. The method for detecting and identifying microbial colonies according to claim 1, wherein said step of eliminating said potential colony if said potential colony is noise around the perimeter of a validated colony comprises the steps of:

a) sorting said potential colonies according to the value of said peak pixel associated with said potential colony;

b) identifying a validated colony closest to said potential colony having the largest peak pixel intensity value;

c) computing a noise radius for said closest validated colony;

d) validating said potential colony if said potential colony is outside said noise radius of said closest validated colony;

e) computing a computed peak value derived from peak pixel values of said potential colony and said closest validated colony;

f) computing a computed radius value derived from radius values of said potential colony and said closest validated colony;

g) validating said potential colony if said computed radius value exceeds a threshold radius value, said computed peak value exceeds a threshold peak value, said peak pixel value of said potential colony exceeds a threshold peak validation value and said radius of said potential colony exceeds a threshold radius validation value; and h) eliminating said potential colony if said potential colony is not a validated colony.

5. The method for detecting and identifying microbial colonies according to claim 4, wherein identifying a closest validated colony comprises the steps of:

a) defining an outer edge of said validated colonies, said outer edge defined by said peak pixel and said colony radius of each said validated colony;

b) defining a potential outer edge of said potential colony, said potential outer edge defined by said peak pixel and said colony radius of said potential colony; and c) labeling said validated colony with said outer edge closest to said potential outer edge of said potential colony as said closest validated colony.

6. A method for detecting and identifying microbial colonies in an inoculated growth medium, said method comprising the steps of:

a) imaging said growth medium to obtain first colony image data;

b) incubating said growth medium for a selected time interval;

c) imaging said growth medium to obtain second colony image data;

d) processing at least one of said images to determine a growth medium center; and e) processing said first and second colony images to produce a difference image wherein said difference image is obtained by taking a difference between said first colony image data and said second colony image data;

f) identifying potential colonies within said difference image, each said potential colony having a peak pixel and a colony radius; and g) validating each said potential colony to ensure said potential colony is a validated colony.

7. The method for detecting and identifying microbial colonies according to claim 6, wherein said growth medium is circular and wherein said step of determining said growth medium center comprises the steps of:

a) performing edge detection in three regions of said image, said regions running substantially between an edge and the center of said first colony image;

b) computing a first midpoint of a first chord between detected edge points in a first region and a second region;

c) computing a second midpoint of a second chord between detected edge points in said second region and a third region; and d) determining a growth medium center, said growth medium center being at the intersection of perpendicular bisectors of said first and second chords.

8. The method for detecting and identifying microbial colonies according to claim 7, further comprising the step of centering a growth medium mask at said growth medium center.

9. The method for detecting and identifying microbial colonies according to claim 7, wherein steps a) through d) are performed a plurality of times to obtain a plurality of growth medium centers further comprising the steps of:

a) selecting all said plurality of growth medium centers within a maximum center distance from each other;

b) determining an averaged growth medium center, said averaged growth medium center being a centroid of said selected growth medium centers; and c) centering a growth medium mask at said averaged growth medium center.

10. A method for detecting and identifying microbial colonies in an inoculated growth medium, said method comprising the steps of:

a) imaging said growth medium to obtain first colony image data;

b) incubating said growth medium for a selected time interval;

c) imaging said growth medium to obtain second colony image data;

d) processing said first and second colony images to produce a difference image wherein said difference image is obtained by taking a difference between said first colony image data and said second colony image data;

e) identifying potential colonies within said difference image, each said potential colony having a peak pixel and a colony radius, by a method comprising the steps of:

i) locating said peak pixel within said difference image, said peak pixel having a local maximum pixel intensity and further exceeding a threshold peak intensity value;

ii) determining gradients from said peak pixel in a predetermined number of directions;

iii) labeling said peak pixel as a potential colony if at least a minimum number of said gradients decrease over a minimum gradient distance;

iv) determining said colony radius for said peak pixel;

v) placing a first mask of predetermined size over said first colony image, said mask centered over said peak pixel; and vi) repeating steps i) through v) for pixels that are not covered by said masks centered over any of said peak pixels; and f) validating each said potential colony to ensure said potential colony is a validated colony.

11. The method for detecting and identifying microbial colonies according to claim 10, wherein said predetermined number of directions to determine gradients is eight.

12. The method for detecting and identifying microbial colonies according to claim 10, wherein locating said peak pixels having said local maximum pixel intensity comprises the steps of:

a) scanning said difference image to locate seed pixels, said seed pixels having an intensity value greater than a threshold seed value;

b) defining a box of predetermined box size;

c) centering the top row of said box over said seed pixel;

d) identifying a maximum box pixel, said maximum box pixel having the largest intensity value within said box, said maximum box pixel being a centroid of several pixels if said several pixels are all pixels having the largest intensity value;

e) repositioning said box over said maximum box pixel, said box centered over said maximum box pixel;

f) repeating steps a) through e) until the number of box moves exceeds a predetermined maximum box move number or said maximum box pixel remains the same in two consecutive repetitions; and g) labeling said maximum box pixel as said peak pixel if said maximum box pixel remained the same in two consecutive repetitions.

13. The method for detecting and identifying microbial colonies according to claim 10, wherein said step of determining a colony radius for said peak pixel comprises the steps of:

a) scanning pixel values in a predetermined number of directions from said peak pixel;

b) computing radius distances for each said direction until said radius distance equals a predetermined maximum radius distance, said pixel value is less than a threshold radius intensity value or said pixel value exceeds the previously scanned pixel value by more than a predetermined noise value; and c) computing the median value of said radius distances for said predetermined number of directions.

14. A method for detecting and identifying microbial colonies in an inoculated growth medium, said method comprising the steps of:

a) imaging said growth medium to obtain first colony image data;

b) incubating said growth medium for a selected time interval;

c) imaging said growth medium to obtain second colony image data;

d) processing said first and second colony images to produce a difference image wherein said difference image is obtained by taking a difference between said first colony image data and said second colony image data;

e) identifying potential colonies within said difference image, each said potential colony having a peak pixel and a colony radius;

f) comparing a peak pixel intensity value of said peak pixel of said potential colony with a spike peak threshold value;

g) comparing said colony radius of said potential colony with a spike radius threshold value;

h) validating said potential colony if said peak pixel intensity value does not exceed said spike peak threshold value or said colony radius exceeds said spike radius threshold value;

i) sorting said potential colonies according to the value of said peak pixel associated with said potential colony;

j) identifying a validated colony closest to said potential colony having the largest peak pixel intensity value;

k) computing a noise radius for said closest validated colony;

l) validating said potential colony if said potential colony is outside said noise radius of said closest validated colony;

m) computing a computed peak value derived from peak pixel values of said potential colony and said closest validated colony;

n) computing a computed radius value derived from radius values of said potential colony and said closest validated colony;

o) validating said potential colony if said computed radius value exceeds a threshold radius value, said computed peak value exceeds a threshold peak value, said peak pixel value of said potential colony exceeds a threshold peak validation value and said radius of said potential colony exceeds a threshold radius validation value; and p) eliminating said potential colony if said potential colony is not a validated colony.

15. A method for detecting and identifying microbial colonies growing on an inoculated growth medium, said method comprising the steps of:

a) incubating said inoculated growth medium for a selected time interval;

b) imaging said growth medium to obtain first colony image data;

c) identifying potential colonies within said first colony image data, each said potential colonies having a peak pixel and a colony radius;

d) validating each said potential colony to ensure said potential colony is a validated colony, by a method comprising the steps of:

i) comparing a peak pixel intensity value of said peak pixel of said potential colony with a spike peak threshold value;

ii) comparing said colony radius of said potential colony with a spike radius threshold value; and iii) eliminating said potential colony if said peak pixel intensity value exceeds said spike peak threshold value and said colony radius does not exceed said spike radius threshold value.

16. A method for detecting and identifying microbial colonies growing on an inoculated growth medium, said method comprising the steps of:

a) incubating said inoculated growth medium for a selected time interval;

b) imaging said growth medium to obtain first colony image data;

c) identifying potential colonies within said first colony image data, each said potential colonies having a peak pixel and a colony radius;

d) validating each said potential colony to ensure said potential colony is a validated colony, by a method comprising the steps of:

i) computing a computed value derived from a peak pixel intensity and a colony radius of said potential colony; and ii) comparing said computed value to a spike peak value; and iii) eliminating said potential colony if said computed value exceeds said spike peak value.

17. A method for detecting and identifying microbial colonies growing on an inoculated growth medium, said method comprising the steps of:

a) incubating said inoculated growth medium for a selected time interval;

b) imaging said growth medium to obtain first colony image data;

c) identifying potential colonies within said first colony image data, each said potential colonies having a peak pixel and a colony radius;

d) validating each said potential colony to ensure said potential colony is a validated colony, by method comprising the steps of:

i) identifying a validated colony closest to said potential colony;

ii) determining a distance from said potential colony to said closest validated colony; and iii) eliminating said potential colony if said distance is less than a predetermined minimum distance.

18. A method for detecting and identifying microbial colonies growing on an inoculated growth medium, said method comprising the steps of:

a) incubating said inoculated growth medium for a selected time interval;

b) imaging said growth medium to obtain first colony image data;

c) imaging said growth medium after a selected time interval to obtain second colony image data;

d) processing said first and second colony images to produce a difference image wherein said difference image is obtained by taking a difference between said first colony image data and said second colony image data, said processing comprising the steps of:

i) locating a peak pixel within said first colony image, said peak pixel having a local maximum pixel intensity and further exceeding a threshold peak intensity value;

ii) determining gradients from said peak pixel in a predetermined number of directions;

iii) labeling said peak pixel as a potential colony if at least a minimum number of said gradients decrease over a minimum gradient distance;

iv) determining a colony radius for said peak pixel;

v) placing a first mask of predetermined size over said first colony image, said mask centered over said peak pixel; and vi) repeating steps i) through v) for pixels that are not covered by said masks centered over any of said peak pixels; and e) identifying potential colonies within said first colony image data, each said potential colonies having a peak pixel and a colony radius; and f) validating each said potential colony to ensure said potential colony is a validated colony.

19. The method for detecting and identifying microbial colonies according to claim 18, wherein locating said peak pixels having said local maximum pixel intensity comprises the steps of:

a) scanning said first colony image to locate seed pixels, said seed pixels having an intensity value greater than a threshold seed value;

b) defining a box of predetermined box size;

c) centering the top row of said box over said seed pixel;

d) identifying a maximum box pixel, said maximum box pixel having the largest intensity value within said box, said maximum box pixel being a centroid of several pixels if said several pixels are all pixels having the largest intensity value;

e) repositioning said box over said maximum box pixel, said box centered over said maximum box pixel;

f) repeating steps a) through e) until the number of box moves exceeds a predetermined maximum box move number or said maximum box pixel remains the same in two consecutive repetitions; and g) labeling said maximum box pixel as said peak pixel if said maximum box pixel remained the same in two consecutive repetitions.

20. A system for detecting and identifying microbial colonies on an inoculated growth medium, said system comprising:

an incubation chamber for incubating said growth medium;

image acquisition means for acquiring images of said growth medium, said image acquisition means acquiring a first colony image at a first time and a second colony image at a second time;

processing means for producing a difference image wherein said difference image is obtained by taking a difference between said first colony image and said second colony image;

means for identifying potential colonies within said difference image, each said potential colony having a peak pixel and a colony radius; and validation means for validating each said potential colony to ensure said potential colony is a validated colony, said validation means comprising means for eliminating said potential colony if said potential colony is a noise spike and means for eliminating said potential colony if said potential colony is noise around the perimeter of a validated colony.

21. The system for detecting and identifying microbial colonies according to claim 20, wherein said means for eliminating said potential colony if said potential colony is a noise spike comprises:

a) means for comparing a peak pixel intensity value of said peak pixel of said potential colony with a spike peak threshold value;

b) means for comparing said colony radius of said potential colony with a spike radius threshold value; and c) means for eliminating said potential colony if said peak pixel intensity value exceeds said spike peak threshold value and said colony radius does not exceed said spike radius threshold value.

22. The system for detecting and identifying microbial colonies according to claim 20, wherein said means for eliminating said potential colony if said potential colony is a noise spike comprises:

a) means for computing a computed value, said computed value derived from a peak pixel intensity and a colony radius of said potential colony; and b) means for comparing said computed value to a spike peak value; and c) means for eliminating said potential colony if said computed value exceeds said spike peak value.

23. The system for detecting and identifying microbial colonies according to claim 20, wherein said means for eliminating said potential colony if said potential colony is noise around the perimeter of a validated colony comprises:

a) means for sorting said potential colonies according to the value of said peak pixel associated with said potential colony;

b) means for identifying a validated colony closest to said potential colony having the largest peak pixel intensity value;

c) means for computing a noise radius for said closest validated colony;

d) means for validating said potential colony if said potential colony is outside said noise radius of said closest validated colony;

e) means for computing a computed peak value derived from peak pixel values of said potential colony and said closest validated colony;

f) means for computing a computed radius value derived from radius values of said potential colony and said closest validated colony;

g) means for validating said potential colony if said computed radius value exceeds a threshold radius value, said computed peak value exceeds a threshold peak ratio value, said peak pixel value of said potential colony exceeds a threshold peak validation value and said radius of said potential colony exceeds a threshold radius validation value; and h) means for eliminating said potential colony if said potential colony is not a validated colony.

24. The system for detecting and identifying microbial colonies according to claim 23, wherein said means for identifying a closest validated colony comprises:

a) means for defining an outer edge of said validated colonies, said outer edge defined by said peak pixel and said colony radius of each said validated colony;

b) means for defining a potential outer edge of said potential colony, said potential outer edge defined by said peak pixel and said colony radius of said potential colony; and c) means for labeling said validated colony with said outer edge closest to said potential outer edge of said potential colony as said closest validated colony.

25. A system for detecting and identifying microbial colonies on an inoculated growth medium, said system comprising:

an incubation chamber for incubating said growth medium;

image acquisition means for acquiring images of said growth medium, said image acquisition means acquiring a first colony image at a first time and a second colony image at a second time;

processing means for producing a difference image wherein said difference image is obtained by taking a difference between said first colony image and said second colony image;

means for identifying potential colonies within said difference image, each said potential colony having a peak pixel and a colony radius;

means for determining a growth medium center of said growth medium; and validation means for validating each said potential colony to ensure said potential colony is a validated colony.

26. The system for detecting and identifying microbial colonies according to claim 25, wherein said growth medium is circular and wherein said means for determining said growth medium center comprises:
   a) means for performing edge detection in three regions of said image, said regions running substantially between an edge and the center of said first colony image;
   b) means for computing a first midpoint of a first chord between detected edge points in a first region and a second region;
   c) means for computing a second midpoint of a second chord between detected edge points in said second region and a third region; and
   d) means for determining a growth medium center, said growth medium center being at the intersection of perpendicular bisectors of said first and second chords.

27. The system for detecting and identifying microbial colonies according to claim 26, further comprising means for centering a growth medium mask at said growth medium center.

28. The system for detecting and identifying microbial colonies according to claim 26, wherein a plurality of growth medium centers are obtained and further comprising:
   a) means for selecting all said plurality of growth medium centers within a maximum center distance from each other;
   b) means for determining an averaged growth medium center, said averaged growth medium center being a centroid of said selected growth medium centers; and
   c) means for centering a growth medium mask at said averaged growth medium center.

29. A system for detecting and identifying microbial colonies on an inoculated growth medium, said system comprising:
   an incubation chamber for incubating said growth medium;
   image acquisition means for acquiring images of said growth medium, said image acquisition means acquiring a first colony image at a first time and a second colony image at a second time;
   processing means for producing a difference image wherein said difference image is obtained by taking a difference between said first colony image and said second colony image;
   means for identifying potential colonies within said difference image, each said potential colony having a peak pixel and a colony radius, wherein said means for identifying potential colonies comprises:
      a) means for locating said peak pixel within said difference image, said peak pixel having a local maximum pixel intensity and further exceeding a threshold peak intensity value;
      b) means for determining gradients from said peak pixel in a predetermined number of directions;
      c) means for labeling said peak pixel as a potential colony if at least a minimum number of said gradients decrease over a minimum gradient distance;
      d) means for determining said colony radius for said peak pixel; and
      e) means for placing a first mask of predetermined size over said first colony image, said mask centered over said peak pixel; and
   validation means for validating each said potential colony to ensure said potential colony is a validated colony.

30. The system for detecting and identifying microbial colonies according to claim 29, wherein said predetermined number of directions to determine gradients is eight.

31. The system for detecting and identifying microbial colonies according to claim 29, wherein said means for locating said peak pixels having said local maximum pixel intensity comprises:
   a) means for scanning said difference image to locate seed pixels, said seed pixels having an intensity value greater than a threshold seed value;
   b) means for defining a box of predetermined box size;
   c) means for centering the top row of said box over said seed pixel;
   d) means for identifying a maximum box pixel, said maximum box pixel having the largest intensity value within said box, said maximum box pixel being a centroid of several pixels if said several pixels are all pixels having the largest intensity value;
   e) means for repositioning said box over said maximum box pixel, said box centered over said maximum box pixel;
   f) means for determining the number of box moves exceeds a predetermined maximum box move number or said maximum box pixel remains the same in two consecutive repetitions; and
   g) means for labeling said maximum box pixel as said peak pixel if said maximum box pixel remained the same in two consecutive repetitions.

32. The system for detecting and identifying microbial colonies according to claim 29, wherein said means for determining a colony radius for said peak pixel comprises:
   a) means for scanning pixel values in a predetermined number of directions from said peak pixel;
   b) means for computing radius distances for each said direction until said radius distance equals a predetermined maximum radius distance, said pixel value is less than a threshold radius intensity value or said pixel value exceeded the previously scanned pixel value by more than a predetermined noise value; and
   c) means for computing the median value of said radius distances for said predetermined number of directions.

\* \* \* \* \*

UNITED STATES PATENT AND TRADEMARK OFFICE
CERTIFICATE OF CORRECTION

PATENT NO.: 5,694,478
DATED: December 2, 1997
INVENTOR(S): Robert A. Braier and Scott D. Morgan It is certified that error appears in the above-identified patent and that said Letters Patent is hereby corrected as shown below:

Column 1, Line 27: Delete the word "used" and insert in place thereof --use--.

Column 8, Line 37: Delete the word "a" before the word "regions".

Column 10, Line 67: Delete the word "the" after "less than".

Column 24, Line 51: Delete the word "exceeded" and insert in place thereof --exceeds--.

Signed and Sealed this

Sixth Day of March, 2001

Attest:

NICHOLAS P. GODICI

Attesting Officer

Acting Director of the United States Patent and Trademark Office